(12) United States Patent
Luxton et al.

(10) Patent No.: US 10,317,345 B2
(45) Date of Patent: Jun. 11, 2019

(54) APPARATUS AND METHOD FOR ANALYSING A SURFACE

(71) Applicants: INTERCEDE VENTURES LTD, Hertfordshire (GB); UNIVERSITY OF THE WEST OF ENGLAND, BRISTOL, Bristol (GB)

(72) Inventors: Richard William Luxton, Bristol (GB); Janice Helen Kiely, Bristol (GB); Timothy Ingram Cox, Bristol (GB); Ben de Lacy Costello, Bristol (GB); Graham Shaun Mimms, Bristol (GB)

(73) Assignees: INTERCEDE VENTURES LTD, Hertfordshire (GB); UNIVERSITY OF THE WEST OF ENGLAND, BRISTOL, Bristol (GB)

( * ) Notice: Subject to any disclaimer, the term of this patent is extended or adjusted under 35 U.S.C. 154(b) by 0 days.

(21) Appl. No.: 15/538,305

(22) PCT Filed: Dec. 21, 2015

(86) PCT No.: PCT/GB2015/054107
§ 371 (c)(1),
(2) Date: Jun. 21, 2017

(87) PCT Pub. No.: WO2016/102945
PCT Pub. Date: Jun. 30, 2016

(65) Prior Publication Data
US 2017/0328841 A1    Nov. 16, 2017

(30) Foreign Application Priority Data

Dec. 22, 2014  (GB) .................................. 1422983.5

(51) Int. Cl.
*G01N 21/00* (2006.01)
*G01N 21/94* (2006.01)
(Continued)

(52) U.S. Cl.
CPC ........... *G01N 21/94* (2013.01); *G01B 11/303* (2013.01); *G01N 21/4738* (2013.01);
(Continued)

(58) Field of Classification Search
CPC ........ G01N 21/94; G01N 21/55; G01N 21/88; G01N 21/00; G01N 21/9501; G01N 21/47;
(Continued)

(56) References Cited

U.S. PATENT DOCUMENTS 5,313,542 A    5/1994  Castonguay
6,097,482 A *  8/2000  Smith ................ G01N 21/8901
                                                        250/237 R
(Continued)

FOREIGN PATENT DOCUMENTS

WO       2004/029674 A2    4/2004

*Primary Examiner* — Hoa Q Pham
(74) *Attorney, Agent, or Firm* — Stuart H. Mayer; Mayer & Williams PC

(57) ABSTRACT

Apparatus for analyzing a surface which, in use, is subject to drag, the apparatus comprising, a light source for generating light of at least one predetermined wavelength, a light source holder for holding and positioning the light source so as to direct it at the surface, a light detector for detecting reflected light from the surface and generating a signal in response thereto, a light detector holder for holding the light detector and positioning it so as to detect the reflected light, and a connector for connecting the light detector to a microprocessor to analyze the signal. Also disclosed is a method of analyzing a surface which, in use, is subject to drag.

21 Claims, 13 Drawing Sheets

(51) Int. Cl.
*G01N 21/47* (2006.01)
*G01N 21/55* (2014.01)
*G01B 11/30* (2006.01)
*G01N 21/88* (2006.01)

(52) U.S. Cl.
CPC ......... *G01N 21/55* (2013.01); *G01N 21/8806* (2013.01); *G01N 2201/06113* (2013.01)

(58) Field of Classification Search
CPC ........... G01N 21/4738; G01N 21/8806; G01N 2201/10; G01B 11/303
USPC ... 356/237.1–237.5, 445–448, 369, 600, 338
See application file for complete search history.

(56) References Cited

U.S. PATENT DOCUMENTS

| | | | |
|---|---|---|---|
| 6,704,101 B1 * | 3/2004 | Rangarajan | G01N 21/47 356/237.2 |
| 2005/0036135 A1 | 2/2005 | Earthman | |
| 2008/0174764 A1 | 7/2008 | Matsui | |

\* cited by examiner

APPARATUS AND METHOD FOR ANALYSING A SURFACE

BACKGROUND OF THE INVENTION

The present invention relates to apparatus and methods for analysing surfaces. In particular, the present invention relates to apparatus and methods for analysing surfaces which, in use, are subject to drag. The present invention also relates to methods for determining surface-related drag of surfaces.

Surfaces that are subject to aerodynamic or hydrodynamic drag are often contaminated by dirt, dust, ice, particulates or other matter present in the environment. The surface may, additionally or alternatively, have intrinsic roughness either because a structure and/or coating with such roughness has been applied (e.g. shark skin-type structures) or because of weathering or abrasion/ablation in the environment (e.g. from particulate impact). Polish may have been applied to modify and smooth surfaces which have developed undesirable roughness. Roughness of the surface or removal of polish by weathering etc. may reveal undesirable surface structure which can lead to increased drag.

Contamination or roughness can adversely affect the performance of surfaces subject to drag. In the case of high speed vehicles such as high speed trains and aircraft, contaminated and/or rough surfaces can increase drag, resulting in higher fuel consumption and can sometimes affect aerodynamics and flight performance. These problems may be particularly troublesome on aircraft surfaces and also wind turbine blades.

Washing of the surfaces to remove contamination, polishing surfaces or otherwise maintaining the surface can be difficult and expensive with large vehicles such as aircraft or difficult to access surfaces such as in wind turbines having to be temporarily taken out of service. Thus maintenance should only be undertaken when necessary. It would therefore be advantageous to determine the extent and effect of the surface structure, for example roughness, polish or contamination, and in particular the effect of the surface structure on drag.

There have been attempts to determine surface conditions, including the extent of the contamination, of surfaces in aircraft and on other aerodynamic surfaces.

EP-A-2 492 195 discloses a technique of ensuring hygienic conditions in interior spaces on board e.g. aircraft.

US-A-2012/085868 discloses an aircraft icing detector using laser probes to determine the surface contour of the depth of airfoil icing in the measurement area.

WO-A-2004/061438 (Boeing) discloses measuring amounts of contaminants on a surface with IR spectroscopy using two or more wavelengths.

EP-A-1 466 827 discloses a fibre optic technique for detecting ice on e.g. a wing or other surface using infrared in the water absorption bands.

There have been other solutions proposed including by treating the aerodynamic surfaces with coatings to change their surface properties.

WO-A-2009/085418 (General Electric) discloses self-cleaning aerodynamic surfaces and the use of coatings to provide such surfaces.

There is, nevertheless, a need to provide apparatus and methods to address these problems.

SUMMARY OF THE INVENTION

In a first aspect, the present invention accordingly provides an apparatus for analysing a surface which, in use, is subject to drag, the apparatus comprising: a) a light source for generating light of at least one predetermined wavelength, b) a light source holder for holding and positioning the light source so as to direct it at the surface, c) a light detector for detecting reflected light from the surface and generating a signal in response thereto, d) a light detector holder for holding the light detector and positioning it so as to detect the reflected light, and e) a connector for connecting the light detector to a microprocessor to analyse the signal.

Such an apparatus is advantageous because it enables surfaces to be analysed (including surface roughness, surface structure or contamination) quickly and simply. The apparatus is such that the surface may be analysed either from close proximity to the surface or in a stand-off mode. This is particularly advantageous where the surface is e.g. a surface of a large aircraft or wind turbine blades.

The apparatus enables analysis of a light spot and/or diffuse illumination on the surface and thus is able to produce data including data relating to the following: spot size; average intensity/grey value; intensity profile of spot, showing various cross sections; maximum intensity; intensity above a threshold; degree of speckling; distribution of speckle intensity; speckle pattern; and/or histograms of intensities in the area of the image.

Such measurements may give an indication of: surface roughness; degree of dirt accumulation; degree of polish applied; and/or the need for cleaning and new polish application.

Usually, the light source holder and/or the light detector holder will be independently movable. Preferably the light source holder and/or the light detector holder will be independently movable so as to be directable at substantially the same portion of the surface to be analysed. Generally and advantageously, the light source holder and/or the light detector holder will be independently pivotable to position the light source and/or the light detector at independent predetermined angles with respect to the surface normal.

A further advantage of the present invention is that the apparatus is flexible in that the reflected light may be generally any scattered light so may be either diffuse reflected light or specular reflected light. Thus, conveniently, the light source may be positioned at an incident beam angle of 0° to 90°, preferably 10° to 80° with respect to the surface normal. Furthermore, the light detector may be positioned at a reflected beam angle of 0° to 80° with respect to the surface normal. In particular or alternatively, the light source and light detector may be positioned to detect light scattering at a glancing angle or to detect back-scattered light. Thus, the light source and/or the light detector may be positioned at an incident beam angle of ±80° to ±90° with respect to the surface normal.

The light source and light detector may be positioned on the same side of the surface normal or on opposing sides of the surface normal. Thus the angle between the light source and light detector may be in the range 0 to $180_{[JK1]}°$, preferably 0 to 170°, more preferably 0 to 150° and most preferably 0 to 130°.

It is useful if the light source is relatively efficient to reduce power consumption. This is particularly advantageous where the apparatus is used from a relatively remote position or location. Consequently, preferably, the light source comprises a light emitting diode.

It is preferred if the light source is adapted to generate collimated light. This is especially beneficial if the apparatus is to be used in stand-off mode where the surface may be at some distance from the light source.

Preferably, especially in stand-off mode, the light source comprises a patterned light source, more preferably a patterned collimated light source. This is advantageous because the pattern can give additional information about the distance between the light source, light detector and surface, the relative angle of the image plane to the object or the angle of the object to the image plane.

A number of patterns may, of course, be used. For example, the pattern may comprise arcs (e.g. twin arcs situated either side of the light source lens) or other curved or angled shapes, for example, the pattern may be circular, oval, or part or whole of any polygonal shape such as a triangle, square or rectangle, pentagon or hexagon.

Alternatively or additionally, the patterned light source may comprise a plurality of light sources (preferably point light sources i.e. each having a diameter of 5 mm or lower) distributed in a predetermined pattern; the distance apart in the image relative to the sensor size may be calibrated to give distance for a given lens. A more complex pattern may also be used such as interlocking circles of light.

Generally, the light pattern may be formed though a pattern plate, preferably a collimated pattern plate, placed in front of a high intensity light source, such as a ring flash or regular stroboscopic light source. The pattern may also be projected onto the surface using a focusing lens.

Preferably, the use of a patterned light source may involve the reflected image of the patterned light being captured by the lens and the intensity of reflected light between the edges of the light source being measured from a normalised grey scale image.

One preferred light source comprises a laser. This is advantageous because of the narrow spectral width of lasers. Use of a laser (or other narrow spectral width light source) may be particularly useful if the detector is intended to detect wavelengths other than the incident wavelength (e.g. to investigate fluorescence from the surface).

Whether or not a laser is used, the light source may also comprise a lens, preferably an adjustable lens.

Usually, the light detector will comprise an image sensor, preferably a charge-coupled device (CCD) array device or a complementary metal-oxide-semiconductor (CMOS) array device.

The, light detector may comprise a lens, preferably a magnifying lens. Such lenses may be, for example, a telephoto lens (this is advantageous in particular for stand-off mode operation) or a macro lens offering a high magnification of the surface). Often, however, a lens will not be required and in those cases, the light detector will not comprise a lens.

The light source may also comprise a neutral density filter to adjust the light output to match the dynamic range of the camera; or to be able to adjust the light output of the LED or laser.

Surprisingly, the inventors have established that it is preferred if the light is visible light. The visible light may be of any particular colour, but excellent results may be obtained by the use of green, red or blue light. Thus, preferably the visible light is selected from one or more of: a) blue light, preferably having a peak wavelength in the range 445 nm to 495 nm, b) green light, preferably having a peak wavelength in the range 495 nm to 570 nm, and/or c) red light, preferably having a peak wavelength in the range 620 nm to 750 nm.

Additionally or alternatively, the light source may use an infra-red wavelength (especially where there is high atmospheric absorption). This may be advantageous because this reduces ambient light interference e.g. from sunlight.

Generally, the wavelength for a particular analysis will usually be chosen to minimize the effect of ambient light, particularly in stand-off mode.

One advantageous feature may be to adapt the apparatus to pulse the light source and gate the detector to take an image with the light source on and then off and subtract the two to reduce background.

Of course, the apparatus may use two or more (for example 3, 4 or 5) wavelengths of light.

The bandwidth of the light is preferably relatively small, more preferably below 50 nm, even more preferably below 30 nm. As discussed above, this may be particularly advantageous where fluorescence analysis is to be undertaken.

To reduce interference with ambient light and otherwise to reduce noise in the signal, it is preferred that the light source and/or the light detector comprise optical filters, preferably polarising optical filters. The light source may be adapted (e.g. through the use of polarising filters) to give either linearly and/or circularly polarized light.

In one embodiment, the band pass filters of the light source and detector may be matched to pass the same wavelength.

Additionally or alternatively, the optical filter on the detector and light source may be different. Such a system is particularly advantageous if fluorescence is to be investigated. In this case, the optical filter on the detector may be at a different wavelength to that of the light source. Fluorescence may be characteristic of dirt, other contamination and/or polish, in particular if the polish has an additive which has a particular fluorescence signature.

Usually, the light source will be adapted to generate a light beam having a diameter in the range 0.5 mm to 5 mm, preferably 1 mm to 3 mm. Thus, a light spot having a diameter of this order of magnitude (taking account of the broadening of a less collimated beam) will be reflected from the surface. This is advantageous because the resolution of the apparatus is thereby improved.

The connector may connect to the microprocessor over a wired or over a wireless system.

The apparatus may transfer or transmit the signal to a remote microprocessor for analysis. Thus, in one embodiment, the apparatus further comprises a microprocessor connected to the light detector.

It is useful if the apparatus further comprises at least one power supply, preferably a battery pack to provide for a portable apparatus e.g. for use in the field.

For some applications, in particular for examination of a surface close to the investigator, the light source, the light source holder, the light detector and the light detector holder, and optionally, the microprocessor and power supply, may be contained within a housing.

In other applications, in particular for stand-off use when examining e.g. aircraft surfaces at a distance from the investigator, the light source and light source holder may be contained in a first housing and the light detector and light detector holder may be contained in a second housing. Each housing may have its own power supply.

In either application, the apparatus may be mounted on a remote controlled vehicle, for example, an unmanned aerial vehicle or drone. If the light source and detector are housed in separate housings, two or more drones may be used, each having one or more housings adapted to allow the mounting on the, or each, drone. Alternatively, one drone carrying either the detector or source may be used together with a land based source or detector.

The light source, light source holder and the light detector and light detector holder may be mounted on a shaft to allow use at distance. The shaft may be rigid or flexible to permit easy control of the direction of the light. This is advantageous because it allows measurement around corners or behind opaque structures.

Preferably, the light source and the light detector may be in a housing and one or more optical fibres optically connected to the light source and the light detector may extend from the housing along an elongate portion (e.g. a shaft or tube). This is advantageous because it allows a user to investigate high surfaces, around corners or behind opaque structures.

It is advantageous if the apparatus further comprises at least one Global Positioning System (GPS) navigation device. Where two (or more) housings are used any or each of the housings may comprise a GPS device. The advantage of GPS navigation is that it allows the user of the apparatus to identify the exact geographical location of the surface. If e.g. commercial aircraft at airport stands are to be examined, GPS enables each particular aircraft to be positively identified and its position and the location of the portion of the surface examined to be recorded.

The great advantage of the present invention is that it enables a method of determining whether a surface is in need of maintenance because for example the surface structure (e.g. roughness) leads to increased drag and/or is contaminated with e.g. dirt. This enables the operator to establish whether the degree of roughness or contamination is likely to increase drag on the surface when the surface is in use. In the case of aircraft, surface related roughness or contamination can result in drag which significantly reduces fuel efficiency or detrimentally affects flight characteristics of the aircraft. In other drag subject surfaces, contamination or roughness can increase drag and thereby reduce efficiency.

Thus, in a second aspect, the present invention provides a method of analysing a surface which, in use, is subject to drag, the method comprising; a) providing a surface which, in use, is subject to drag, b) generating a light beam of at least one predetermined wavelength, c) directing the light beam on to a portion of the surface to form a light spot or an illuminated area, d) detecting the intensity of the reflected light across the light spot or the illuminated area, and e) comparing the intensity of the reflected light at positions across the light spot or illuminated area, thereby analysing the surface.

The method may be used on generally any surface subject to drag. The surface may be, for example, a surface of a propeller blade or a turbine blade or a vehicle. The method is particularly advantageous when the vehicle is an aircraft, especially a commercial aircraft, a water vessel (or example a ship, boat or submarine) or a land vehicle. The method is of general utility.

One use of the method is for determining the contamination of a surface. The contamination may comprise, for example, ice, dirt, dust, oil, grit, other particulates and/or insects or other organic matter (e.g. bird droppings).

Alternatively or additionally, the method may be used for determining the roughness of a surface. The roughness may be from abrasion or ablation in the environment, other wear, weathering, change in polish on the surface or from intentional structuring of the surface using e.g. a coating.

The method will usually further comprise measuring the incident beam angle and/or the angle of reflection with respect to the surface normal.

Additionally, the method will often further comprise stabilising the position of the light spot or illuminated area and/or adjusting the intensity of the light spot or illuminated area.

Generally, detecting the intensity of the reflected light will comprise identifying the location of the light spot or illuminated area, and acquiring the image of the light spot or illuminated area.

The method may further comprise c1) producing a profile of intensity against a distance axis across the light spot. Furthermore, the method may further comprise e) generating a threshold value that is higher than an intensity that can be recorded from a comparative surface and f) summing the light intensity values greater than the threshold value for all points along the distance axis.

Many of the optional and preferred features of the second aspect of the invention correspond to those of the first aspect with appropriate modification as would be understood by the skilled person.

As discussed herein, identifying and quantifying roughness or contamination of a drag susceptible surface is advantageous because it enables an investigator to establish whether contamination or roughness is likely to increase drag of the surface in use.

Consequently, in a third aspect, the present invention provides a method of determining surface-related drag on a surface, the method comprising; a) analysing at least a portion of the surface according to the second aspect, b) determining the surface structure on the portion of the surface, c) optionally, determining the surface energy of the portion of the surface, d) selecting a drag value model, e) applying the drag value model to the surface structure and, optionally, the surface energy, and f) generating a drag factor associated with the surface.

Preferably the method further comprises g) relating the drag factor to likely reduction in fuel consumption for the vehicle.

The surface energy of the portion of the surface may conveniently be determined by a step comprising measuring the contact angle of a liquid droplet, preferably a water droplet, on the portion of the surface. Generally, a high water contact angle indicates a hydrophobic surface and a low water contact angle indicates a hydrophilic surface.

Other information may be incorporated in the determination of drag for example empirical data relating types and degree of surface structure or contamination to drag of a surface.

Many of the optional and preferred features of the third aspect of the invention correspond to those of the first and second aspects with appropriate modification as would be understood by the skilled person.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention.

It is to be noted that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B.

Reference throughout this specification to "an embodiment" or "an aspect" means that a particular feature, structure or characteristic described in connection with the embodiment or aspect is included in at least one embodiment or aspect of the present invention. Thus, appearances of the phrases "in one embodiment", "in an embodiment", or "in an aspect" in various places throughout this specification are not necessarily all referring to the same embodiment or aspect, but may refer to different embodiments or aspects. Furthermore, the particular features, structures or characteristics of any embodiment or aspect of the invention may be combined in any suitable manner, as would be apparent to one of ordinary skill in the art from this disclosure, in one or more embodiments or aspects.

Similarly, it should be appreciated that in the description various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Moreover, the description of any individual drawing or aspect should not necessarily be considered to be an embodiment of the invention. Rather, as the following claims reflect, inventive aspects lie in fewer than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some features included in other embodiments, combinations of features of different embodiments are meant to be within the scope of the invention, and form yet further embodiments, as will be understood by those skilled in the art. For example, in the following claims, any of the claimed embodiments can be used in any combination.

In the description provided herein, numerous specific details are set forth. However, it is understood that embodiments of the invention may be practised without these specific details. In other instances, well-known methods, structures and techniques have not been shown in detail in order not to obscure an understanding of this description.

In the discussion of the invention, unless stated to the contrary, the disclosure of alternative values for the upper or lower limit of the permitted range of a parameter, coupled with an indication that one of said values is more highly preferred than the other, is to be construed as an implied statement that each intermediate value of said parameter, lying between the more preferred and the less preferred of said alternatives, is itself preferred to said less preferred value and also to each value lying between said less preferred value and said intermediate value.

BRIEF DESCRIPTION OF THE DRAWINGS

In the accompanying drawings.

DETAILED DESCRIPTION OF THE INVENTION

Figure 1A:
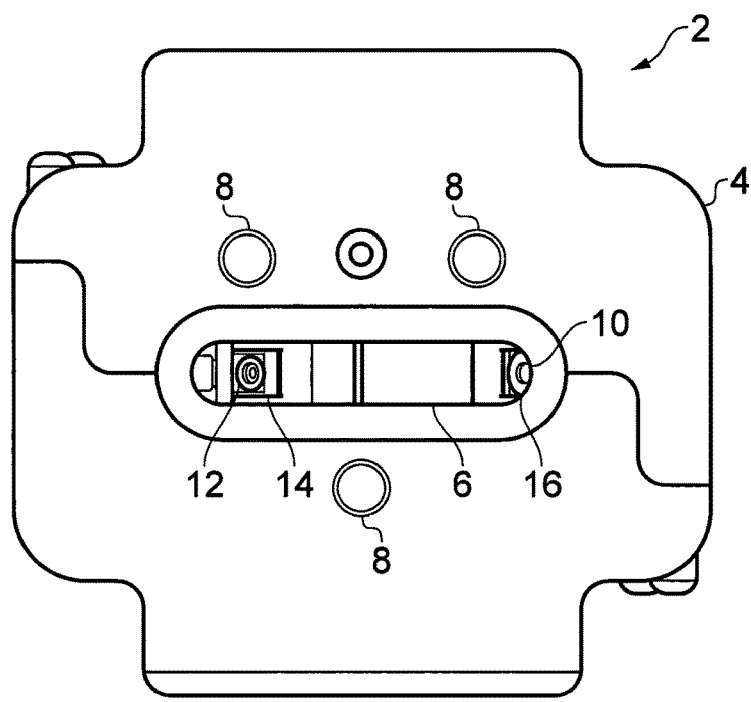
FIG. 1(a) illustrates a bottom view of apparatus according to an embodiment of the present invention.

FIG. 1(a) shows the bottom view of an embodiment of the apparatus 2 for determining surface contamination. The apparatus 2 is designed with a housing 4 having in its bottom portion a sensor aperture 6 through which the light source 12 (in this case a blue laser of peak wavelength 445 nm) which is mounted in the housing 4, may shine through a polarising source filter 14. Light reflected from the surface (not shown) to be investigated is detected by light detector 10 (in this case a CCD camera), also mounted in the housing 4, after passing through a detector polarising filter 16.

The apparatus 2 has three adjustable legs 8, arranged so that the height and orientation of the sensor aperture 6 (and hence light source 12 and light detector 10) may be controlled when the apparatus is situated on a surface to be investigated.

Figure 1B:
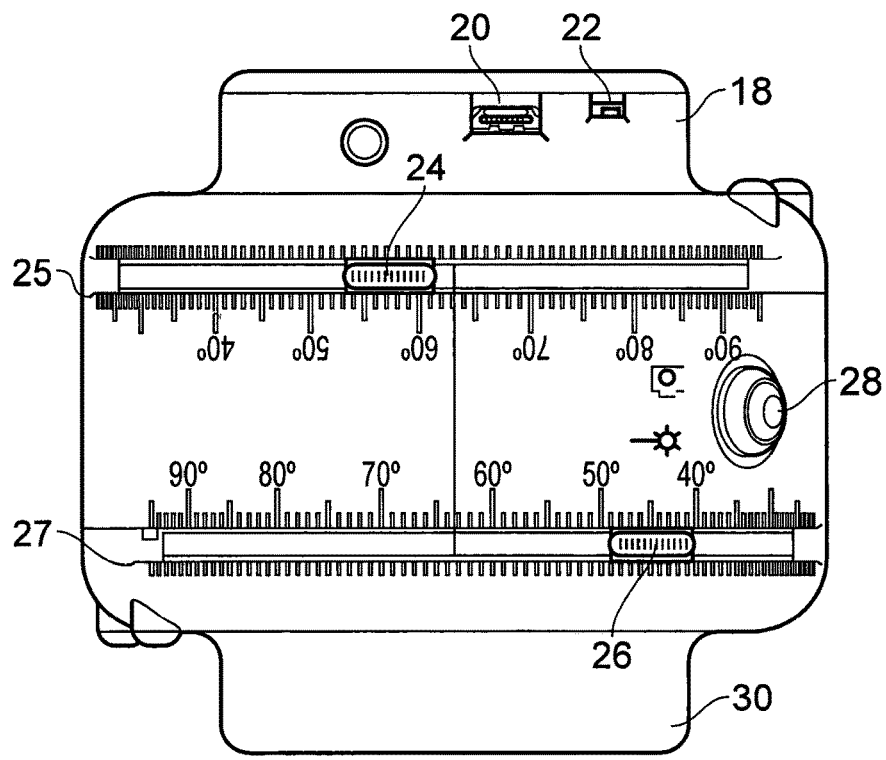
FIG. 1(b) illustrates a top view of the apparatus illustrated in FIG. 1(a).

The top view of the apparatus 2 is shown in FIG. 1(b). The apparatus has a light source slider 26 and a light detector slider 24 connected to the light source holder (not visible in FIG. 1(b)) and light detector holder (also not visible in FIG. 1(b)) respectively. The sliders 24, 26 enable the angle of the light detector 10 and light source 12 to be adjusted independently. The detector angle scale 25 and source angle scale 27 connected to the light detector holder and light source holder respectively, enable an investigator to determine and manually set the required angle for each.

A microprocessor holder 18 forms part of one side of the housing 4 and contains a microprocessor to analyse the detector signal. The microprocessor holder 18 contains USB connector 20 and SD connector 22 for connecting the microprocessor of the apparatus 2 to other equipment. At the other side of the housing 4 to the microprocessor holder 18 there is a power supply holder 30 which contains the battery pack to power the apparatus 2. A start button 28 is also situated on the housing 4.

Figure 1C:
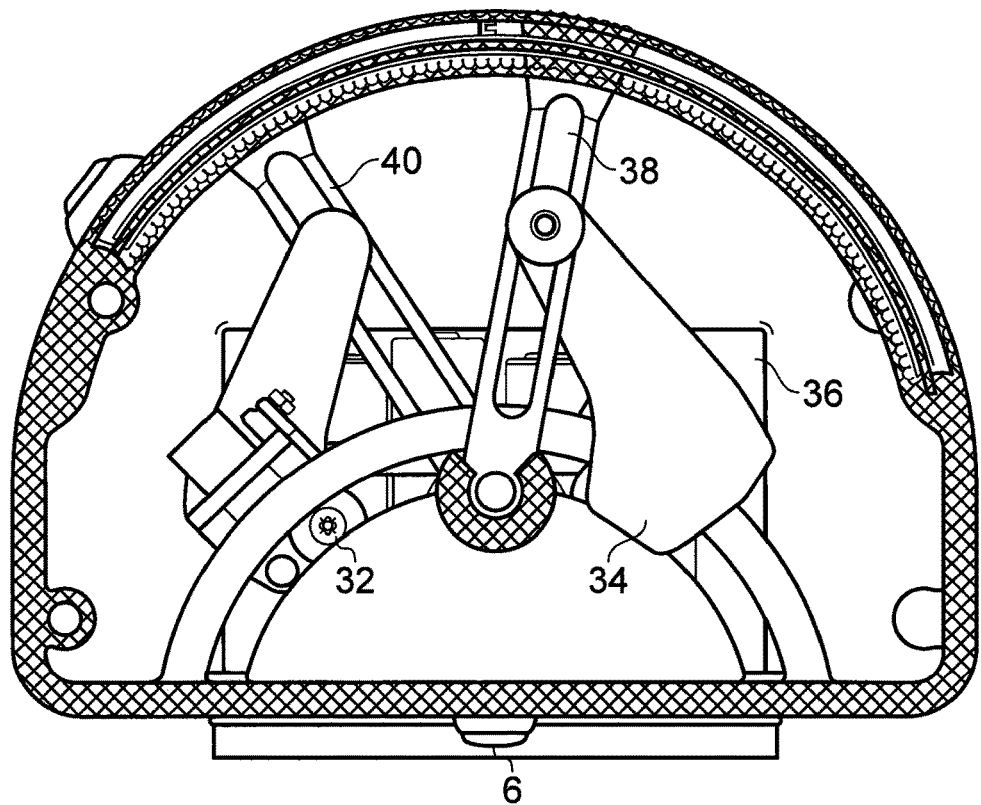
FIG. 1(c) illustrates a side cross sectional view of the apparatus illustrated in FIG. 1(a), with the cover removed to show the working parts.

FIG. 1(*c*) shows a cross sectional side view through the apparatus 2. The detector holder 34 is connected to a detector lever 38 which pivots on movement of the detector slider 24, thereby changing the angle of the light detector 10 (not visible in FIG. 1(*c*)). Similarly, the source holder 32 is connected to a source lever 40 which pivots on movement of the source slider 26, thereby changing the angle of the light source 12 (not visible in FIG. 1(*c*)). Thus, the angle of the beam generated by the light source 12 and passing through the sensor aperture 6 can be varied independently of the angle of the light detector 10.

Figure 3:
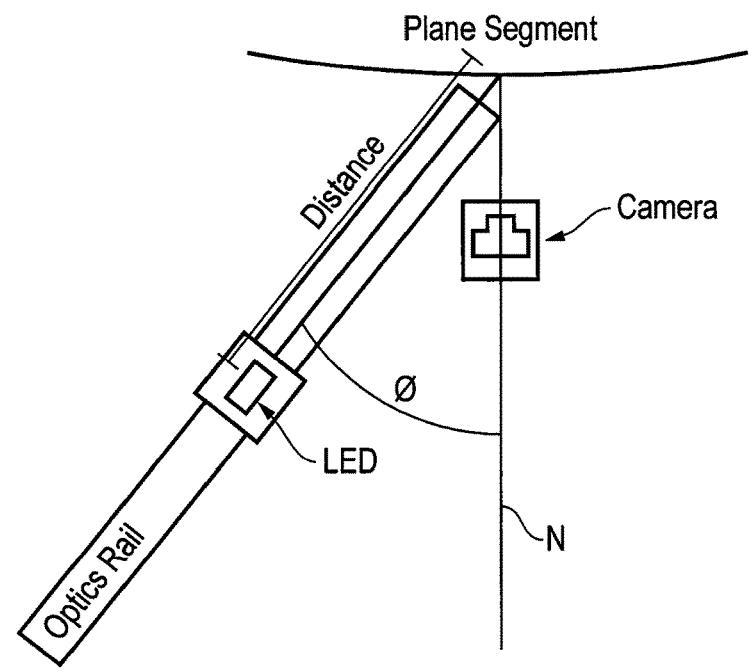
FIG. 3 is a diagram illustrating the protocol of Experiment 1, below.

FIG. 3 illustrates the arrangement of equipment to conduct Experiment 1, described below. An LED light source (no additional collimation) situated on an optics rail generates a light beam incident on a portion of the surface of aircraft at an angle ϕ with respect to surface normal N. A detector is situated normal N to the surface. This angle of incidence is effectively constant over the small area of the surface which is imaged by the camera.

Figure 9:
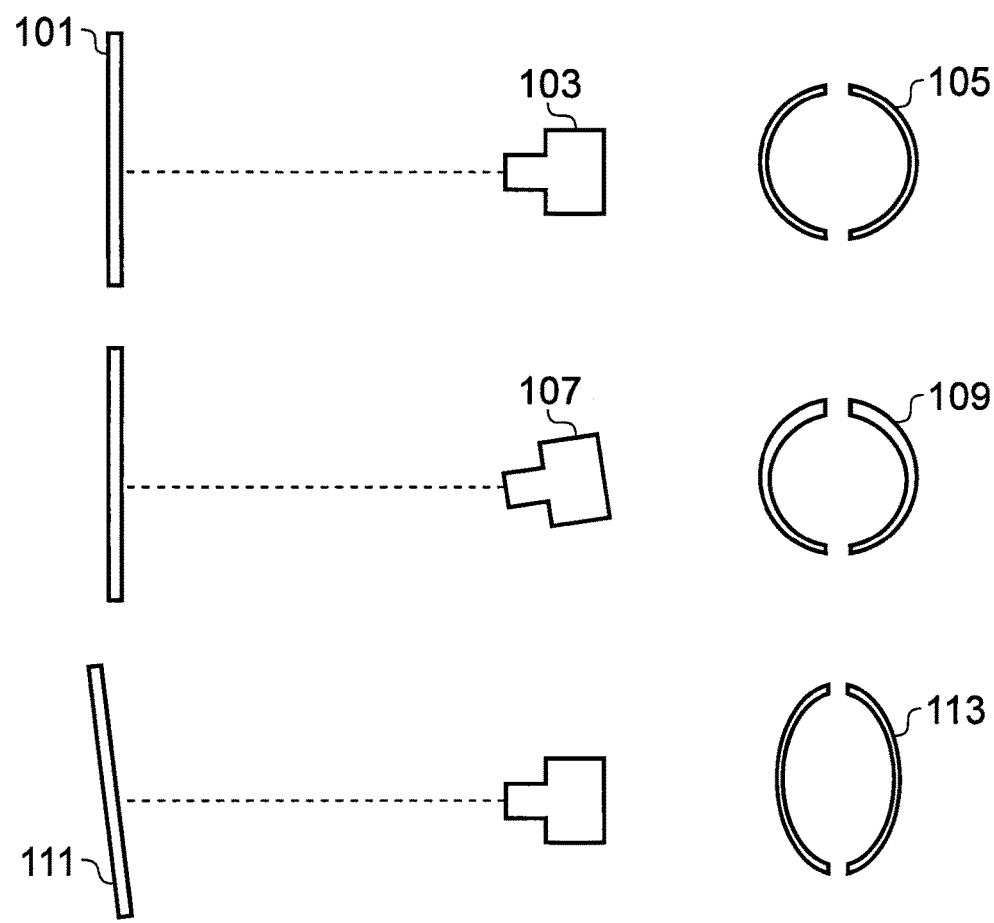
FIG. 9 shows schematically the use of a patterned light source to determine relative angle and distance of light source and surface.

FIG. 9 shows schematically the use of a patterned light source to determine relative angle and distance of light source and surface. The patterned light source is a pattern of two arcs (twin arc pattern) on either side of the lens of the light source. Other patterns may, of course, be used. For example the pattern could be circular, oval, or any polygon shape such as a triangle, square or rectangle, pentagon or hexagon. The pattern may also or alternatively comprise a plurality of light sources (e.g. point light sources) at predetermined distances from each other, the distance apart in the image relative to the sensor size may be calibrated to give distance for a given lens. A more complex pattern may also be used such as interlocking circles of light. Generally, the light pattern may be formed though a collimated pattern plate placed in front of a high intensity light source, such as a ring flash or regular stroboscopic light source. The pattern could also be projected onto the surface using a focusing lens.

The surface being studied 101 perpendicular to the light source 103 produces, in the detector, a non-distorted image 105 of the twin arc pattern. When the light source 107 is at an angle relative to the surface 101, a distorted image 109 of the twin arc pattern is produced indicative of the angle. Similarly, when the surface 111 is at an angle relative to the light source a different distorted image 113 of the twin arc pattern is produced, again indicative of the angle. The size of the pattern image relative to the size of the source pattern indicates the distance between the surface 101 and the light source 103 for a known distance using a focusing lens of a known focal length.

Experiment 1.
Sample: clean painted planar section of an aircraft
There were two regions on the sample:
Region 1—clean
Region 2—an area with an oily film with representative 'dirt'.
Illumination—a green LED (532 nm) at different distances, d, with no additional focussing optics.
The data produced is thus an image of part of the aircraft under green illumination.
The specific conditions of measurement were as follows:
Camera at 90 degrees to surface
Laser at 30 degrees
Camera Make—Canon
Model—Canon EOS 7D
Resolution Unit—Inch
Exposure Time—1/50 seconds
F-number—11
ISO Speed Ratings—200
Exposure Bias Value—0
Focal Length of lens—50 mm
Color Space—sRGB
Exif Image Width—5184
Exif Image Height—3456
White Balance—Auto
Camera to surface distance: approx 30 cm.

A 2D intensity map, i.e. the reflected green LED intensity at different pixels is the output as shown in FIG. 4(*a*). The dirt spot is in the centre of the plot labelled A in FIG. 4(*a*).

The larger peaks to the left of the plot are due to reflections of the window light—the plane is quite reflective.

Figure 4A:
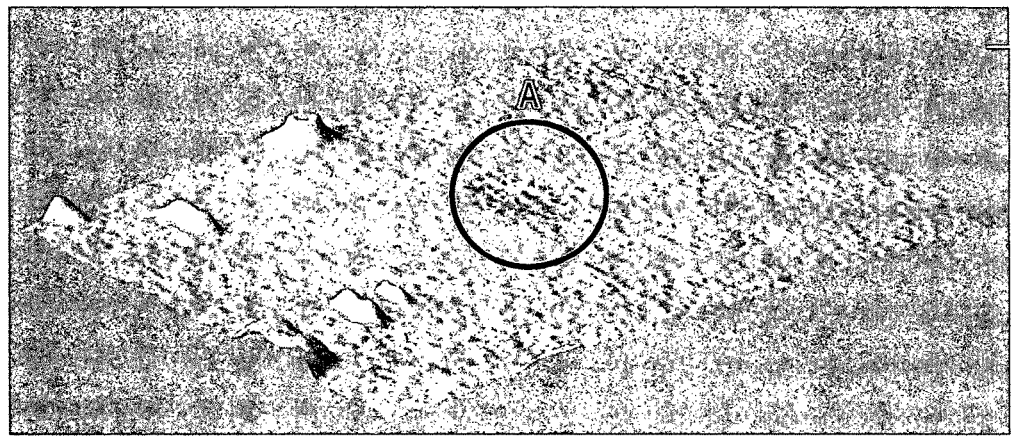
FIG. 4(a) is a 3D plot of intensity of the image at each pixel for the dirty surface of Experiment 1.
Figure 4B:
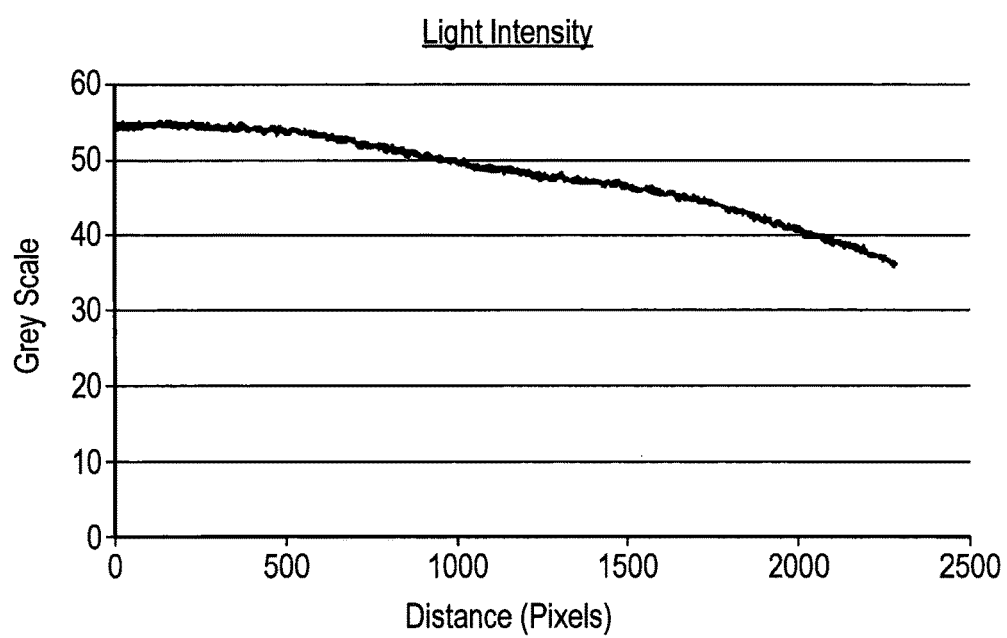
FIG. 4(b) is a graph of grey scale (illumination from 120 mm) as a function of distance (pixels) of a line scan of the intensity across regions of the image for the clean area (Experiment 1).
Figure 4C:
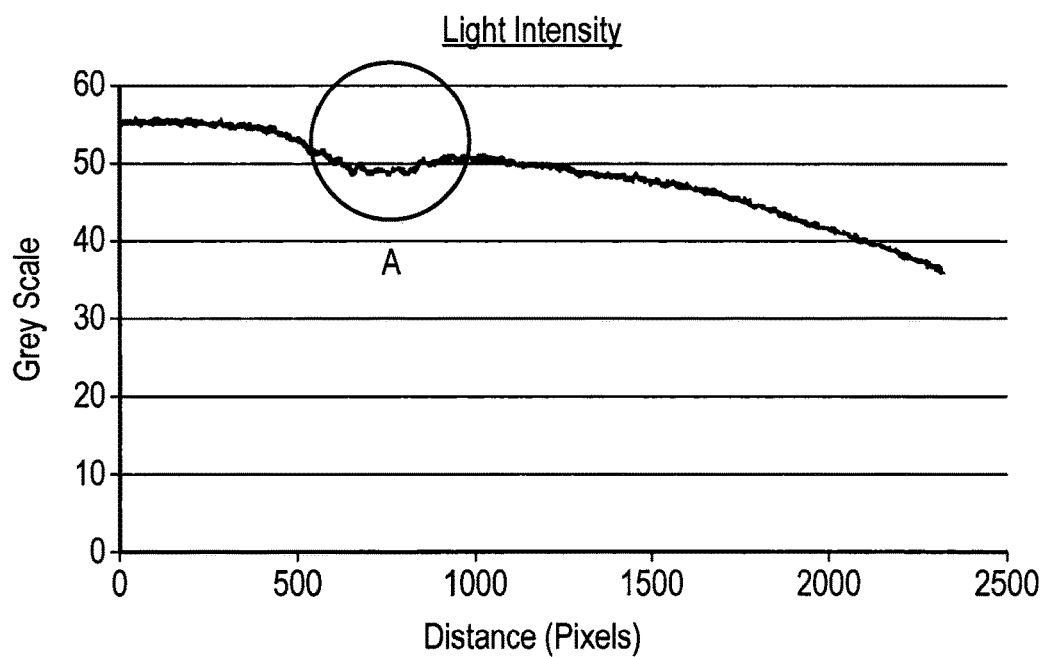
FIG. 4(c) is a graph of grey scale (illumination from 120 mm) as a function of distance (pixels) of a line scan of the intensity across regions of the image for the dirty area (Experiment 1).
Figure 4D:
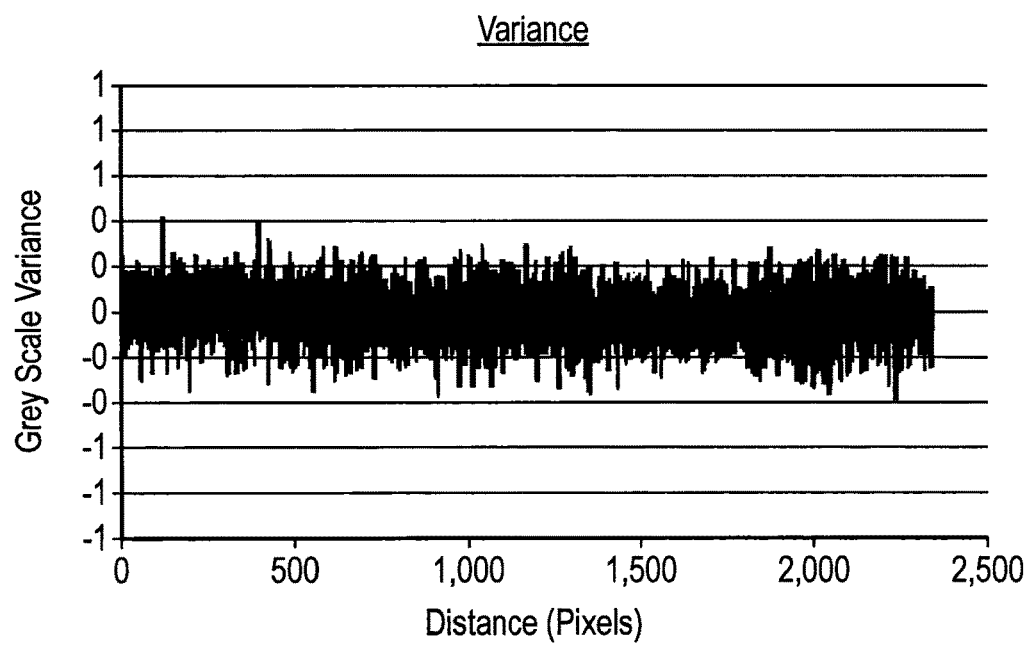
FIG. 4(d) is a graph of variance as a function of distance (pixels) for FIG. 4(b).
Figure 4E:
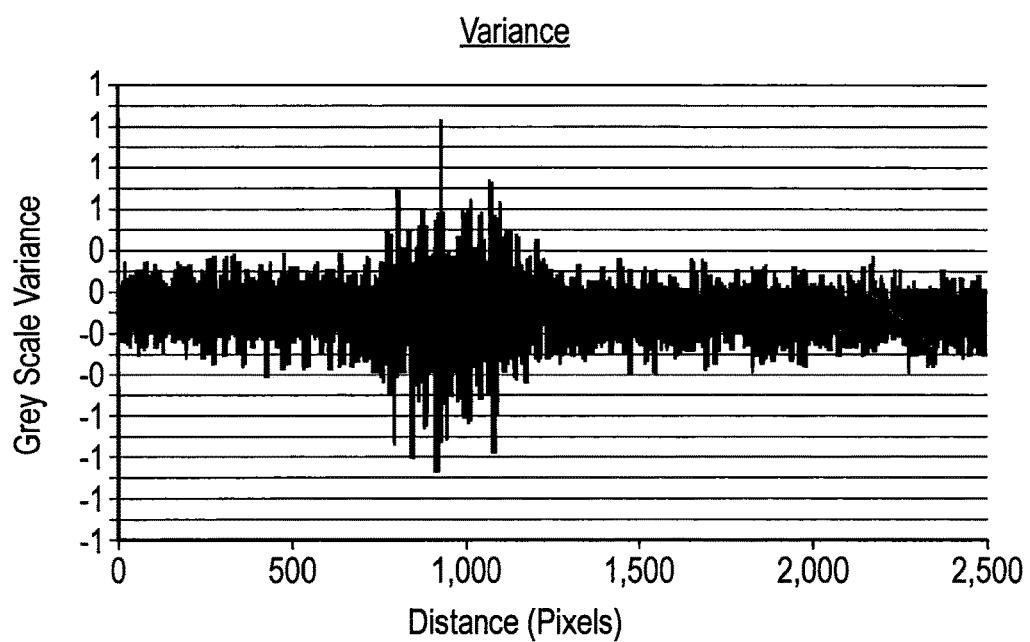
FIG. 4(e) is a graph of variance as a function of distance (pixels) for FIG. 4(c).

Other results—for illumination from 120 mm—the closest distance used as shown in FIGS. 4(*b*) and 4(*c*) and are line scans of the intensity across regions of the image of the plane, FIG. 4*b*) for the clean region, FIG. 4(*c*) the dirty region.

The smooth variation in intensity for both clean and dirty regions is due to the non-uniform illumination from the LED.

In addition to the smooth intensity variation seen for the clean surface, there is a dip in intensity in the region corresponding to the dirt spot. The scan for the dirty area (indicated as A in FIG. 4(*c*)) being through the centre of the dirt spot.

The intensity changes rapidly locally where there is granularity in the surface, e.g. due to particles or variation in the dirt. Thus one approach to analysis is to look at the change in intensity between neighbouring pixels, as shown in the FIGS. 4(*d*) and 4(*e*) graphs of variance in grey scale as a function of (pixel) distance.

In the clean region in FIG. 4(*d*), there is some noise in change between adjacent pixels for a line scan. In the dirty region as shown in FIG. 4(*e*) the increased noise around 1000 pixels reflects the granularity in the image due to the structure within the dirty area.

Experiment 2

Experiment 2 was generally similar to Experiment 1—but here there is a lens in front of the LED. The lens is placed to give a collimated beam. Thus, if the beam has low divergence it would be suitable to give stand-off illumination.

Sample: clean painted planar section of an aircraft
Region 1—clean
Region 2—an area with an oily film with representative 'dirt'.
Illumination—a green LED (532 nm) at different distances, d, with a focussing lens which is at a fixed distance from the led to give a collimated beam.
Camera—focussed on the surface at a distance of 20 cm.

Figure 5:
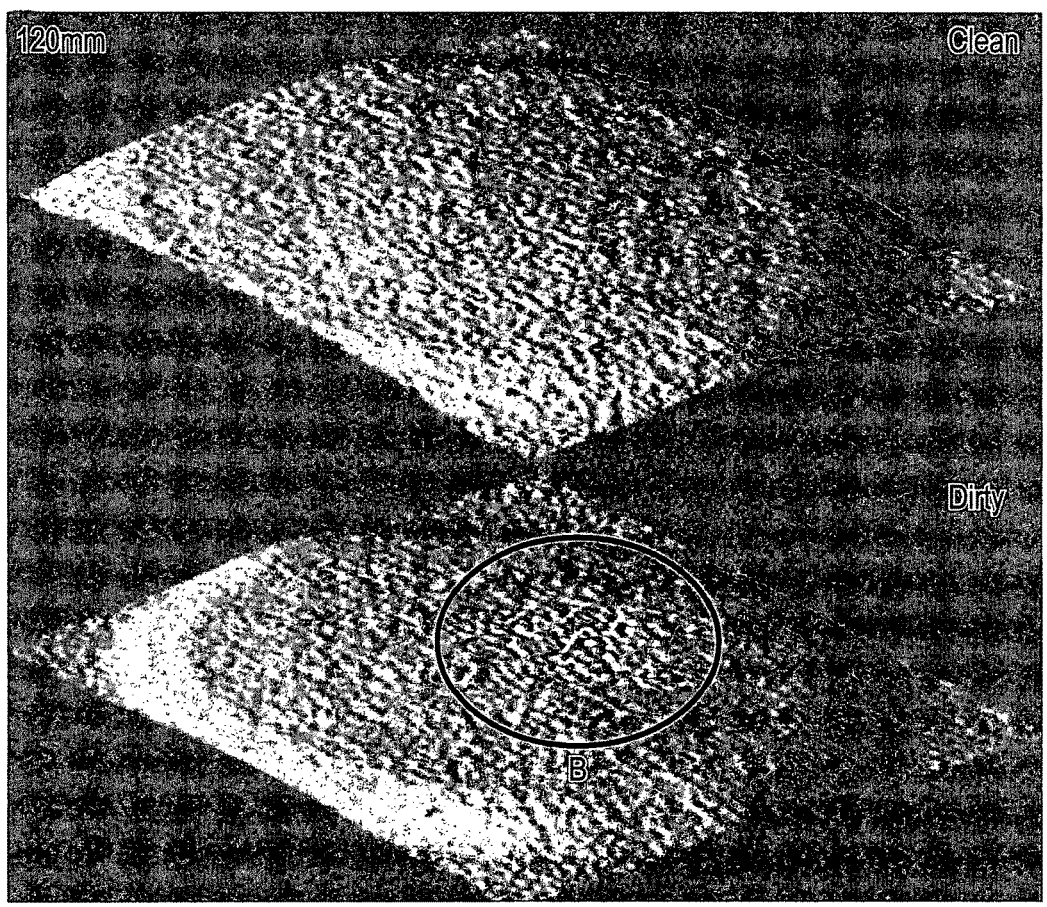
FIG. 5 is a 3D plot of intensity of the image at each pixel for the clean and dirty surfaces of Experiment 2.
Figure 6:
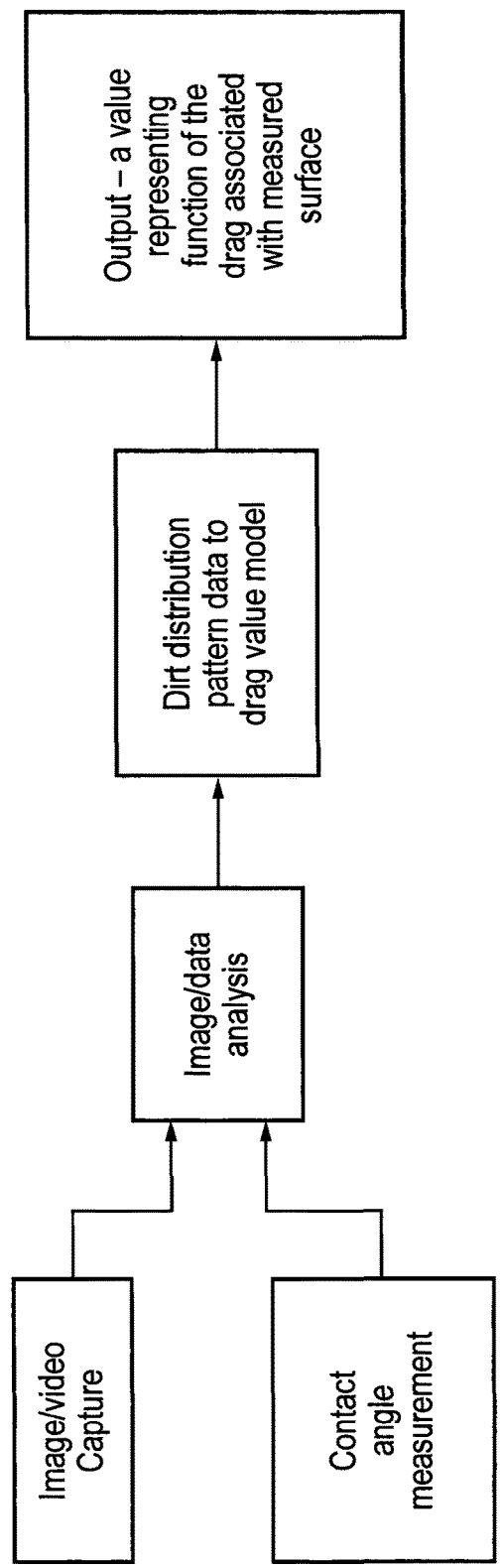
FIG. 6 is a flow diagram showing the method for determining drag associated with a surface.
Figure 7:
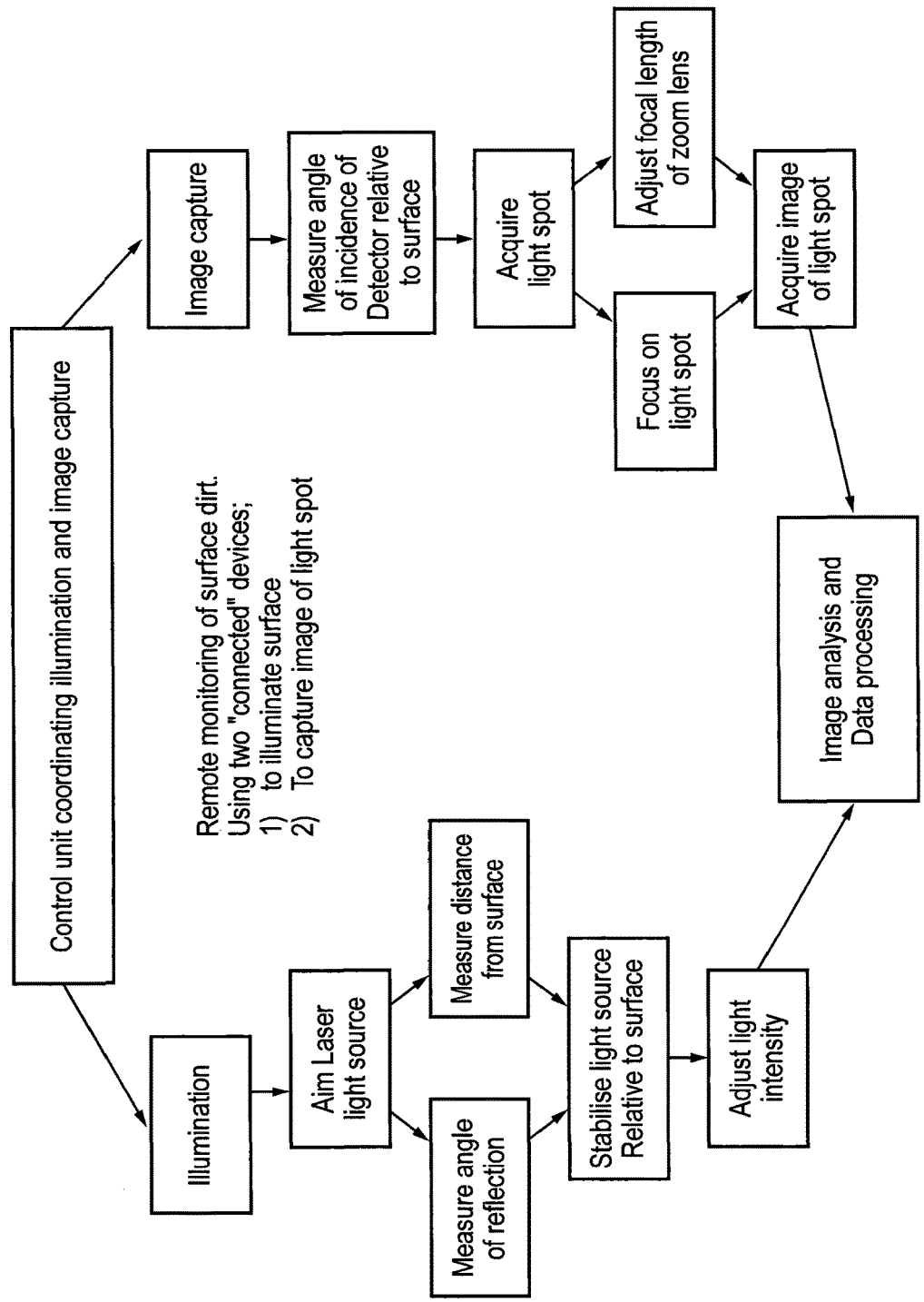
FIG. 7 is a flow diagram showing the method.

FIG. 5 illustrates a 2D intensity map. The dirty area (indicated by B in FIG. 5) and granularity in the image can be seen as in Experiment 1.

Experiment 3

This experiment used abrasive paper as these provide rough surfaces with particles of generally known dimensions—both lateral and in height. A range of abrasive papers is available offering a wide range of characteristic dimensions. Images were recorded with laser illumination. No lens was used for collimation, offering an approximately parallel beam over the small area of the image.

The camera focussed well at this short distance. The spacing between pixels was measured for each camera distance and zoom setting. This allows us to relate the distance measured in pixels to spatial dimensions on the imaged surface. This allowed correlation of the image with the grit size of abrasive paper.

FIG. 8 *a*) to *d*) shows the results of imaging the abrasive paper samples and consists of histograms of grey scale as a function of pixel distance along the line of measurement. FIG. 8 *e*) shows the result of imaging a mirror surface as a comparator.

This experiment shows that the apparatus according to the invention is useful for determining particle size of contaminants or surface structures which (as discussed below) may be related to drag.

Example 1

For remote monitoring according to the invention there is generally a need to capture an image of the light spot on the surface of the aeroplane or other structure to be analysed. The light will generally be aimed at the surface at an angle between 0 or 1 and 90 degrees from normal. This light source may be ground based or situated on a drone. A detector will generally capture an image of the light spot or pattern on the surface being investigated. A telephoto lens system will generally be used to focus the image on the sensor in such a way that the image of the light spot or pattern will fill a proportion, for example 60%, of the sensor capture area. The sensor may be ground mounted or mounted on a drone. The light source and detector may be in separate units, which can be moved independently. Preferably, the light source is collimated and may be one or more monochromatic light sources (e.g. a laser) or white light.

Method

A rig was constructed consisting of two optical rails, post holders, lens holders, a light source and a camera. A red laser (650 nm±10 nm, <1 mW) or blue LED were used as the light source. In both cases the light source was approximately 50 cm from the surface to be measured. The light source was placed adjacent to a lens holder with a matched pair of achromatic lenses (100 mm; 100 mm). For the laser this produced a diffuse circular spot of 25 mm diameter. For the blue LED this set up produced a circular spot of light approximately 30 mm in diameter. The camera (Infinity 2.1 Lumenera, with 18-108 mm macro zoom lens) was mounted behind and above the light source and focussed on the light spot. A low exposure time of typically 1-10 ms was used for the camera to avoid saturation of the light density in the relevant channels.

The test surfaces were three samples with low, medium and high levels of synthetic dirt applied to the surface. These surfaces were illuminated with a red laser at normal incidence and the image of the illuminated area recorded with the camera at an angle of 30° to the surface normal. A line scan of the intensity across the image of the illuminated spot was recorded. The area under the curve of the line scan across the illuminated spot region was integrated for both the red and green channels for the different levels of synthetic dirt. The results are indicated in Table 1 below showing integrated intensities for red and green channels.

TABLE 1

|  | Low Contamination | Medium Contamination | High Contamination |
| --- | --- | --- | --- |
| Red Channel Intensity (arb units) | 2437 | 1770 | 543 |
| Green Channel Intensity (arb units) | 132 | 36 | 0 |

Threshold Method

A number of methods may be used to determine surface structure, one important method of analysis uses a threshold method.

There is a relationship between surface roughness and the intensity of reflected light as shown at least by Experiment 3 above. The relationship may be quantified by taking the intensity above a threshold level which has the effect of reducing the background scatter from a smooth surface and measuring increasing light scatted by increasing roughness on a surface. Granularity can be seen in the image which relates to particle sizes. Generally, dirt or other contamination on the surface reduces the amount of light scatter.

Figure 8A:
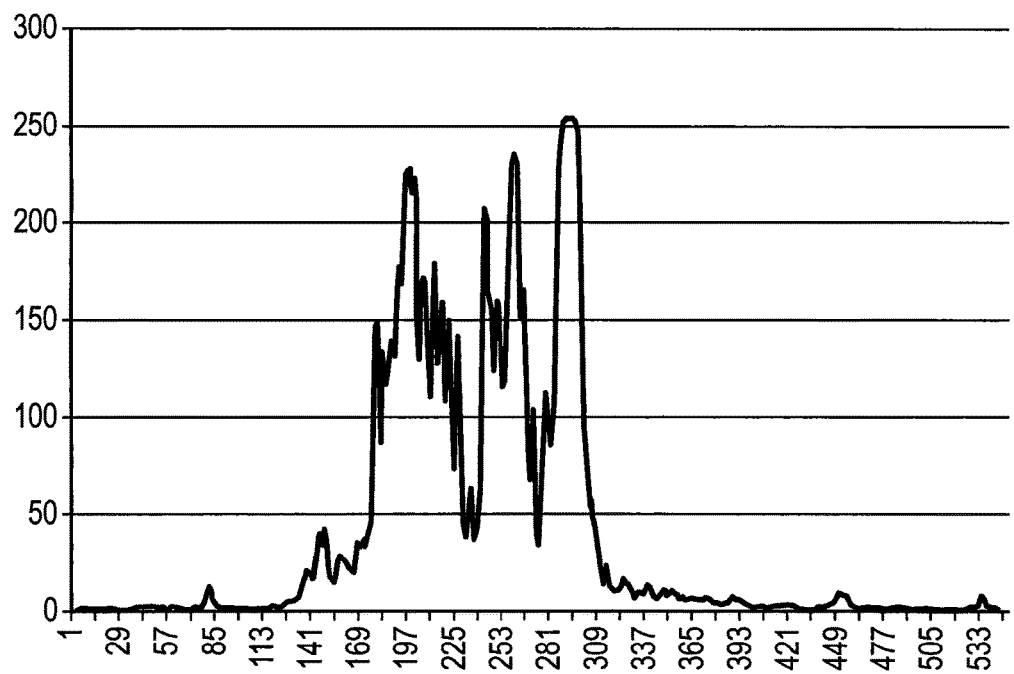
FIG. 8 a) to e) show histograms of grey scale against pixel distance for light spots of abrasive sheets as discussed below, where the mean particle size of the abrasive particles is (a) 162 µm, (b) 59 µm, (c) 35 µm, (d) 22 µm, (e) mirror surface.
Figure 8B:
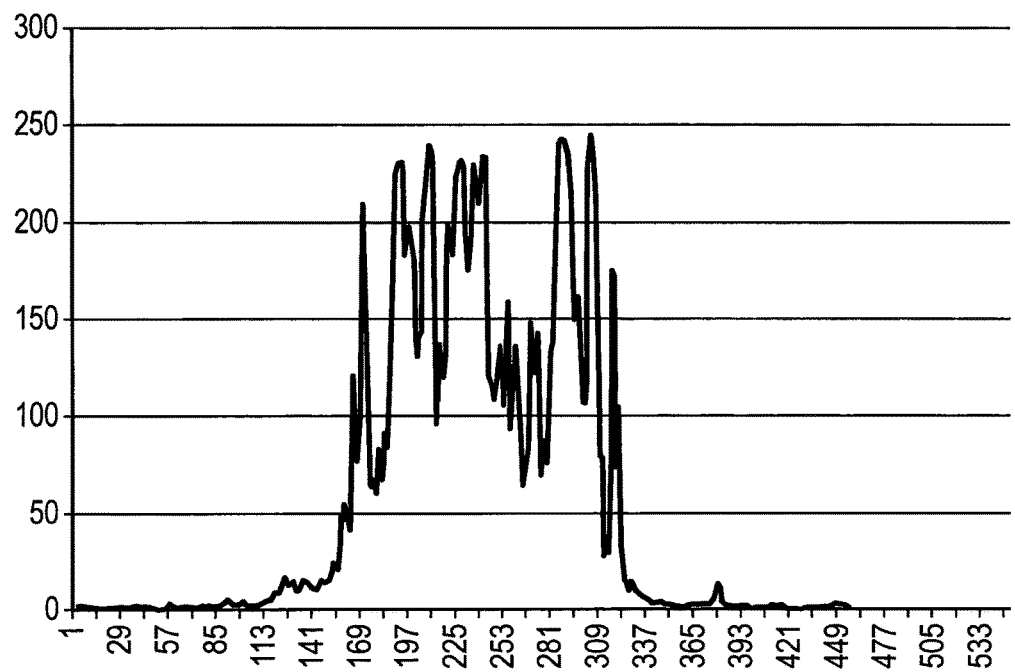
Figure 8C:
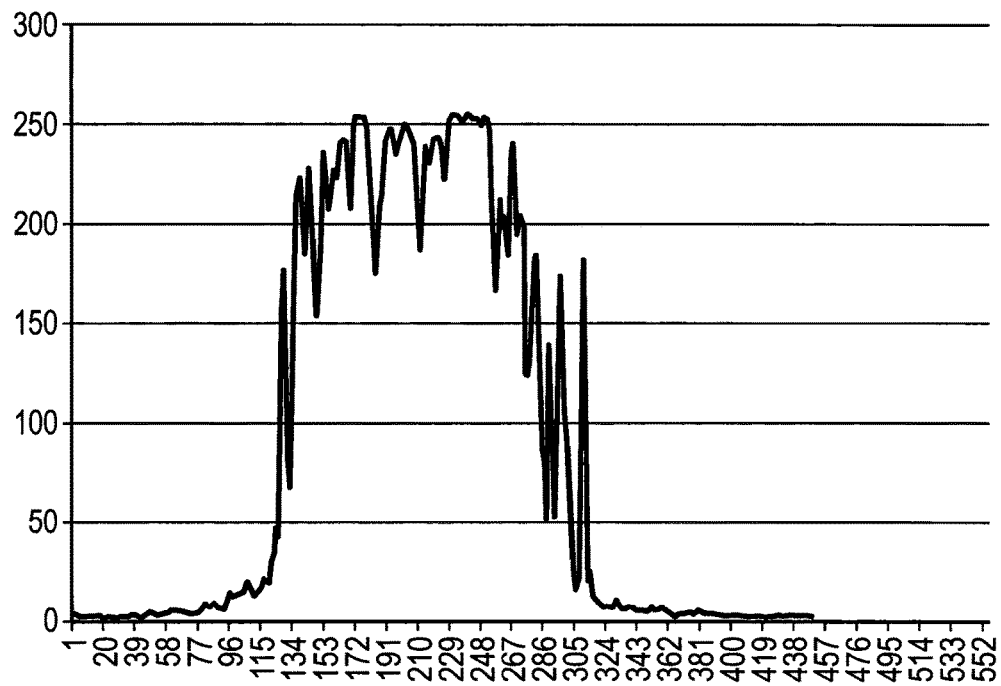
Figure 8D:
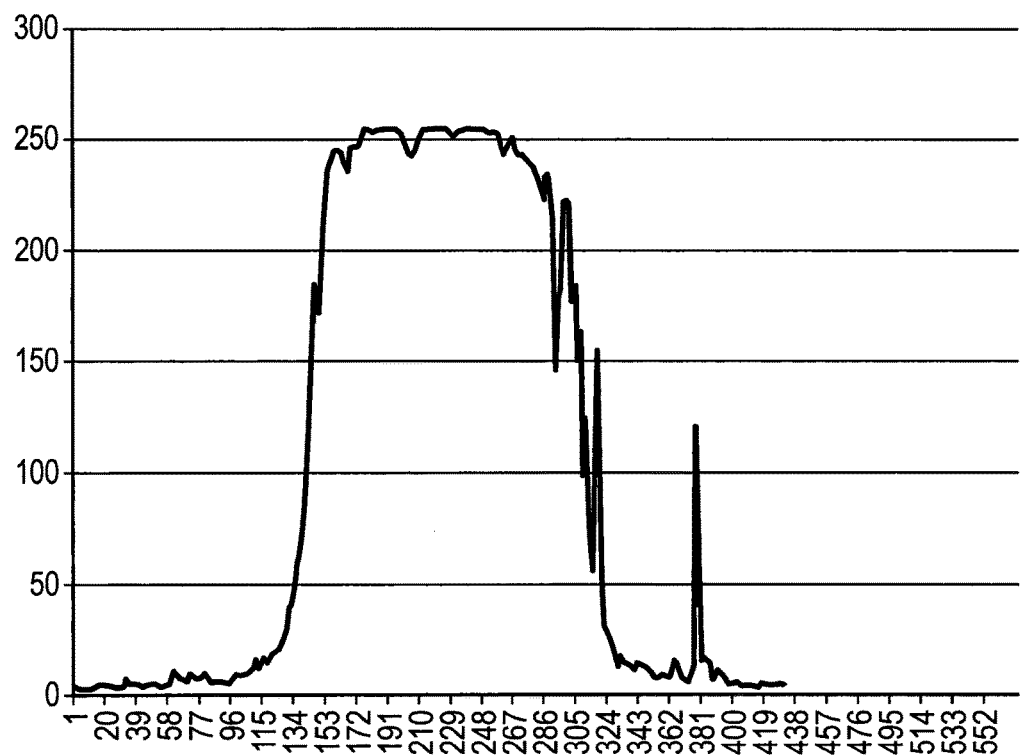
Figure 8E:
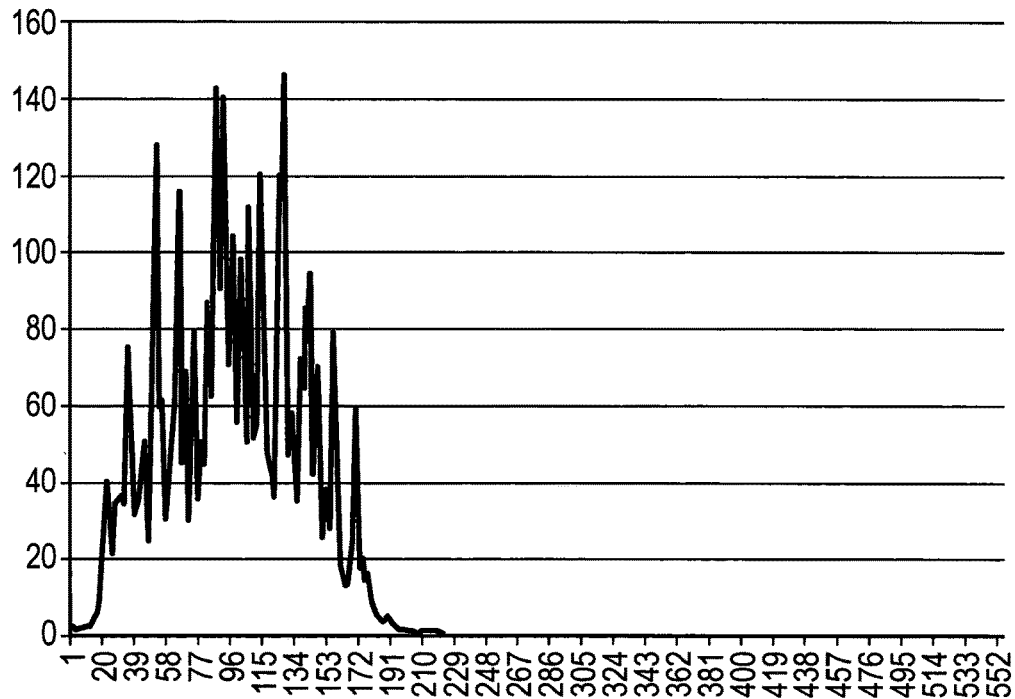

The threshold may be determined for particular surfaces according to the following protocol:
1) Capture spot image
2) Resize image
3) Normalise pixel intensities of image
4) Map spot shape
5) Acquire pixel intensity for a cross section of spot image (different cross sections can be used)
6) Produce profile of pixel intensity against measure of distance along spot
7) Create a threshold (cut off value) that is higher than an intensity that can be recorded from a mirrored surface (see for example FIG. 8, in particular the mirror surface of FIG. 8*e*). The threshold value chosen will depend on colour of surface.
8) Sum the light intensity values greater than the threshold value for all points along the distance axis.

The final value may be used to correlate with roughness and/or dirtiness based on previous calibrations. This enables a determination to be made of the surface structure and hence an analysis of the surface.

Method Using a Patterned Light Source

A stand-off measurement was made using a camera system with an attached ring flash and patterned aperture covering the front of the ring flash and camera. Lenses of differing focal lengths could be used to give different working distances for the stand-off measurement.

Example 2

Results of reflected light from a rough surface and a reflective surface pre and post cleaning are shown in Table 2 below. The stand-off distance was 1.5 m using a 135 mm lens on a cropped sensor which equates to about 202 mm.

The light source was a xenon ring flash attached to the font of the 135 mm lens with a patterned aperture mounted over the ring flash in such a way that the lens could capture images through a central aperture of 50 mm.

This was surrounded by another two apertures to form a pattern of light on the surface. In this case, the apertures were two opposing segments of a 75 mm circle, each 5 mm wide.

The flash was triggered and an image was taken of the surface. The camera was carefully positioned so to capture an image of the reflection of the patterned light on the surface. The exposure was adjusted to capture light from the ring flash and not the ambient light. The image was converted to a grey scale and normalised and then the average pixel intensity of the central disc between the reflected arcs of light was recorded.

TABLE 2

| Nature of Surface | Mean Grey Value (arb. Units) | Standard Dev. Gray Value (arb. Units) |
| --- | --- | --- |
| Rough | 132 | 41 |
| Dirty | 61 | 22 |
| Clean | 20 | 8 |

Example 3

Results of reflected light from a side panel of a black car pre and post cleaning are shown in Table 3. Measurement were taken at midday with an overcast sky. The stand-off distance was 1.5 m using a 135 mm lens on a cropped sensor which equates to about 202 mm.

The system used was the same as described in example 2 above.

TABLE 3

| Nature of Surface | Mean Grey Value (arb. Units) | Standard Dev. Gray Value (arb. Units) |
| --- | --- | --- |
| Dirty | 74 | 8 |
| Clean | 12 | 3 |

Example 4

Figure 10:
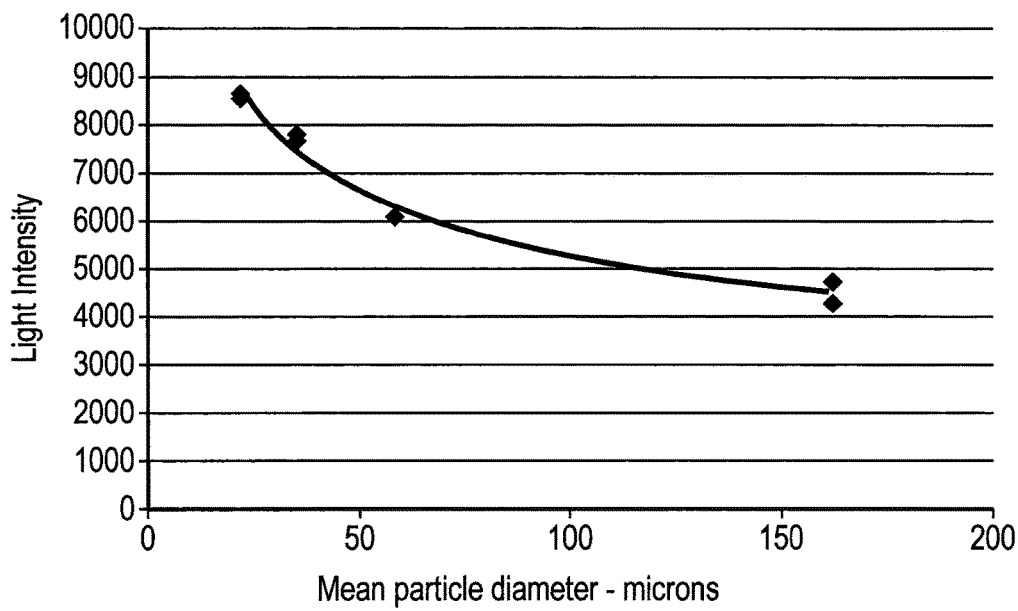
FIG. 10 is graph showing correlation between the sum of the light intensities under the curve and the average particle diameter (measurements all done in triplicate) as used in Example 10.

Procedure for determining the drag of an aircraft surface of unknown mean particle size Two portions of aerofoil surface were evenly coated with dirt of undefined mean particle size—one with larger and one with smaller particles. Both surfaces were measured using the protocol of Experiment 3 to provide plots of grey scales against pixel distance across the light spot and then the threshold method was used to determine the light intensity for each case. Using the calibration plot of FIG. 10 the corresponding mean particle size was calculated. Subsequently the plot of FIG. 2 was used to relate the particle size to provide a figure for the drag associated with each surface. Table 4 below shows light intensity and mean particle size and drag determined using this method.

TABLE 4

| | Light intensity | Mean Particle diameter | Drag (N) |
| --- | --- | --- | --- |
| Surface A | 7085 | 43 microns | 50.6 |
| Surface B | 5374 | 89 microns | 50.85 |

Relating Surface Cleanness to Drag

Figure 2:
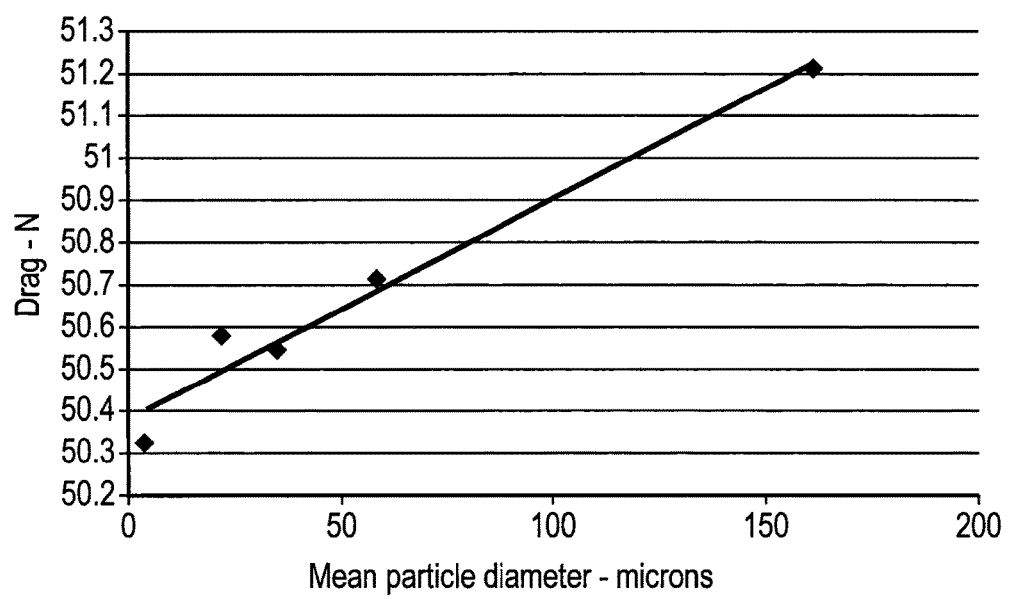
FIG. 2 is a graph of drag as a function of mean particle diameter for particles on the surface.

Dirt or increases in roughness of a surface may result in an increase in drag for given surface size and shape and air speed. This is a result of increased turbulence of the boundary layer. This is demonstrated using wind tunnel experiments. FIG. 2 shows that for a given number of particles as the number of particles increase the drag increases. In addition different dirt particle distribution may result in different drag values.

Relating Surface Polish to Drag

A polished surface can provide reduced drag. So in a similar manner to that described above the inventive apparatus (optionally with contact angle measurements) may be used to determine the quality of the polish on a surface. The quality of polish on a surface relates to the drag thus enabling determination of the drag value for a particular surface in an air flow.

The invention claimed is:

1. A method of analysing a surface which, in use, is subject to drag, the method comprising;
    a) generating a light beam of at least one predetermined wavelength,
    b) directing the light beam on to a portion of the surface to form an illuminated area,
    c) detecting the intensity of the reflected light across the illuminated area,
    c1) producing a profile of intensity against a distance axis across the illuminated area,
    d) comparing the intensity of the reflected light at positions across the illuminated area, thereby analysing the surface,
    e) generating a threshold value that is higher than an intensity that can be recorded from a comparative surface and
    f) summing the light intensity values greater than the threshold value for all points along the distance axis.

2. A method as claimed in claim 1, wherein the surface is a surface of a propeller blade or a turbine blade or a vehicle.

3. A method as claimed in claim 2, wherein the vehicle is an aircraft, a water vessel or a land vehicle.

4. A method as claimed in claim 1, wherein the method is for determining the contamination of a surface and the contamination comprises ice, dirt, dust, oil, grit, other particulates and/or organic matter.

5. A method as claimed in claim 1, wherein the method is for determining the roughness of a surface.

6. A method as claimed in claim 1, further comprising measuring the incident beam angle and/or the angle of reflection with respect to the surface normal.

7. A method as claimed in claim 1, further comprising stabilising the position of the illuminated area.

8. A method as claimed in claim 1, further comprising adjusting the intensity of the illuminated area.

9. A method as claimed in claim 1, wherein detecting the intensity of the reflected light comprises identifying the location of the illuminated area, and acquiring the image of the illuminated area.

10. A method as claimed in claim 1, wherein the reflected light is diffuse reflected light.

11. A method as claimed in claim 1, wherein the reflected light is specular reflected light.

12. A method as claimed in claim 1, wherein the light beam is generated by a light source positioned at an incident beam angle of 0° to 90° with respect to the surface normal.

13. A method as claimed in claim 1, wherein the detecting is performed using a light detector positioned at a reflected beam angle of 0° to 80° with respect to the surface normal.

14. A method as claimed in claim 1, wherein the light beam is generated by a patterned light source.

15. A method as claimed in claim 14, wherein the patterned light source comprises a curved or angled pattern.

16. A method as claimed in claim 14, wherein the patterned light source comprises a plurality of light sources distributed in a predetermined pattern.

17. A method as claimed in claim 1, wherein the detecting is performed using a light detector comprising a charge-coupled device (CCD) camera or a complementary metal-oxide-semiconductor (CMOS) sensor camera.

18. A method as claimed in claim 1, wherein the detecting is performed using a light detector comprising a magnifying lens.

19. A method for determining surface related drag of a surface, the method comprising;
   a) analysing at least a portion of a surface which, in use, is subject to drag, by
      i) generating a light beam of at least one predetermined wavelength,
      ii) directing the light beam on to a portion of the surface to form an illuminated area,
      iii) detecting the intensity of the reflected light across the illuminated area,
      iv) comparing the intensity of the reflected light at positions across the illuminated area, thereby analysing the surface,
   b) determining the surface structure on the portion of the surface,
   c) determining the surface energy of the portion of the surface,
   d) selecting a drag value model,
   e) applying the drag value model to the surface structure and the surface energy, and
   f) generating a drag factor associated with the surface.

20. A method as claimed in claim 19, further comprising
   g) relating the drag factor to likely reduction in fuel consumption for the vehicle.

21. A method as claimed in claim 19, wherein determining the surface energy of the portion of the surface comprises measuring the contact angle of a liquid droplet on the portion of the surface.

* * * * *